US005970155A

United States Patent [19]

Leppälahti

[11] Patent Number: 5,970,155
[45] Date of Patent: Oct. 19, 1999

[54] HEADSET FOR HEARING PROTECTORS

[75] Inventor: Kai Leppälahti, Kauniainen, Finland

[73] Assignee: Kitek Oy Ab Insinooritoimisto, Espoo, Finland

[21] Appl. No.: 08/799,223

[22] Filed: Feb. 14, 1997

[30] Foreign Application Priority Data

Aug. 16, 1996 [FI] Finland .................................... 963234

[51] Int. Cl.[6] ........................................ A61F 11/06

[52] U.S. Cl. ............................ 381/72; 381/370; 381/375; 381/378; 379/430; 455/149

[58] Field of Search ............................ 381/183, 187–188, 381/309, 375, 371, 374, 300, 327, 370, 378, 72; 379/430; 455/149, 344

[56] References Cited

U.S. PATENT DOCUMENTS 2,353,070 7/1944 Pitkin ...................................... 379/430

*Primary Examiner*—Curtis A. Kuntz
*Assistant Examiner*—Duc Nguyen
*Attorney, Agent, or Firm*—Birch, Stewart, Kolasch & Birch, LLP

[57] ABSTRACT

The invention relates to a headset (1) for a hearing protector provided with a padding part (12) having an essentially elliptical ear opening (18). The headset comprises a microphone (2), an earphone (3), and conducting wires (7) for bringing signals to the earphone (3) and from the microphone (2). According to the invention the earphone (3) is attached to a bow part (10) whose contour essentially follows the external dimensions of the hearing protector padding (12), and a mounting wing (13, 4) is connected to the bow part (10) or the earphone (3) and has a maximum dimension (A) which is smaller than the maximum dimension of the ear opening (18) and yet greater than the minimum dimension (B) of the ear opening (18), and during use the maximum dimension of the mounting wing (13, 4) is essentially horizontal.

4 Claims, 5 Drawing Sheets

HEADSET FOR HEARING PROTECTORS

BACKGROUND OF THE INVENTION

1. Field of the Invention

The invention relates to a headset for hearing protectors according to the preamble of claim 1.

2. Description of Background Art

Maintaining on-line radio telephone communication in situations necessitating the use of different kinds of protectors, such as hearing protectors and respirators as well as helmets and protective clothing, is difficult, or, in fact, almost impossible without auxiliary equipment. The term 'auxiliary equipment' refers to an earphone/microphone combination coupled with a built-in speaker and microphone in the radiotelephone or used to replace these altogether. Such combined microphones and earphones have been used almost since radio telephones became available. They have been manufactured by both radio telephone manufacturers and specialized companies. The best-known user groups include air pilots as well as drivers of military vehicles and signallers. Used by civilians, such combinations have become more common along with the increased use of radio telephones and wireless and line telephones.

The above-mentioned increased use of protectors and protective clothing as well as the need for a hands-free mode for reasons of occupational safety impose new requirements on the compatibility of the combinations in different work situations. Thus far, commercially manufactured built-in earphone/microphone combinations have been available in hearing protectors. The manufacturers of such combinations have themselves almost invariably been manufacturers of hearing protectors.

The following features are characteristic of such prior art hearing protectors equipped with a microphone and an earphone:

a) The cups of the hearing protectors are pressed over the user's ears by means of the springback force generated by the bow connecting them;

b) The inside of the cups is provided with a sound-absorbing material, usually expanded plastic, and depending on the size of the cup and the amount of said material, different degrees of damping are attained depending on the audio frequency in question;

c) The edge of the cup is rimmed with a annular, typically elliptic padding which during use closes the inside of the cup against the user's cheek.

The aforementioned fixedly mounted earphone/microphone combinations (headsets) in the protective cups necessitate changes, namely piercing, machining, and glueing, etc., to be performed on the cups and the bow. Such units are manufactured in various European countries, the USA, Japan and South Korea.

Headsets of the above-described kind are mainly hampered by their complexity and expensiveness, where a restricted supply limits competition. As manufacturers only provide integral units, each alternating user requires personal equipment even where only momentary use occurs.

Other prior-art solutions applied in combination with hearing protectors are based on an earphone in the user's ear equipped with a wire between the padding and the user's cheek. In such solutions, the microphone is constituted by the following a) a laryngophone (throat microphone) fixed to a collar worn round the user's neck. The disadvantage here is that the earphone is placed in the auditory canal where it as a result of prolonged use causes irritation and requires hygienic measures to be taken. In order to function in a satisfactory manner, the laryngophone requires a certain pressure and careful adjustment into position which in turn often results in discomfort during use.

b) A separate microphone attached to the user's collar as close to his/her mouth as possible, whereby such a microphone needs to be of the noise compensated kind so as to perform in noisy conditions, and whereby the microphone needs to be placed such that background sounds reach the microphone from all directions. The drawback involved herein, in addition to the above-cited problems related to the earphone itself, lies with the risks of the separate wires being exposed to unwanted traction.

c) The earphone itself which from inside the ear captures acoustic vibration transmitted from the vocal chords to the ear cavity through cavities in the head. When transmitting, the weak signal generated in the ear capsule requires amplification and its frequency pattern needs to be modified to comply with the transmitter modulator. In addition to the above-cited problems relating to the earphone, the solution is hampered by the amplifier structure, protection, and current supply. Regardless of the drawbacks, this solution is a practical and simple one in short-term use.

d) A separate microphone placed in the same piece with the earphone and responding to the vibration of the ear bone. The weak signal requires amplification and its frequency pattern must be modified to comply with the modulator of the radio telephone transmitter. The drawbacks and advantages are as cited under c).

Integral headsets generally referred to as "light headsets" are as such not fitted for use with hearing protectors due to either their mechanical structure or the fact that they impair the noise abatement properties of the hearing protectors.

SUMMARY OF THE INVENTION

The invention is based on connecting the microphone and the earphone to each other by means of a stiff body part which follows the outer contour of the hearing protector padding, and the headset is mounted by means of a rotatable tongue arrangement which is seated between the hearing protector padding and the body part. Thus the headset according to the invention is mounted straight into the hearing protector cup regardless of protector type. The headset is advantageously equipped with a noise compensated microphone and a compact high-performance earphone which fits all types of radiophones, and can during the manufacturing stage be equipped with another type of microphone.

The invention provides considerable benefits:

The advantage involved in the headset according to the invention is its easy use with a standard hearing protector without any need for altering or modifying the hearing protector itself.

By means of the headset the radiotelephone user can freely receive incoming calls and voice messages and, correspondingly, send messages without removing the hearing protector or leaving the noise area.

Due to the inventive solution the user can be granted the possibility to receive calls and to maintain radiotelephone communication at location under all conditions necessitating the use of hearing protectors independent of the make and structure of the protector (bow over the top of the user's head or round the back of his neck, attachable to a helmet or foldable).

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention being thus described, it will be obvious that the same may be varied in many ways. Such variations are not to be regarded as a departure from the spirit and scope of the invention, and all such modifications as would be obvious to one skilled in the art were intended to be included within the scope of the following claims.

Figure 1:
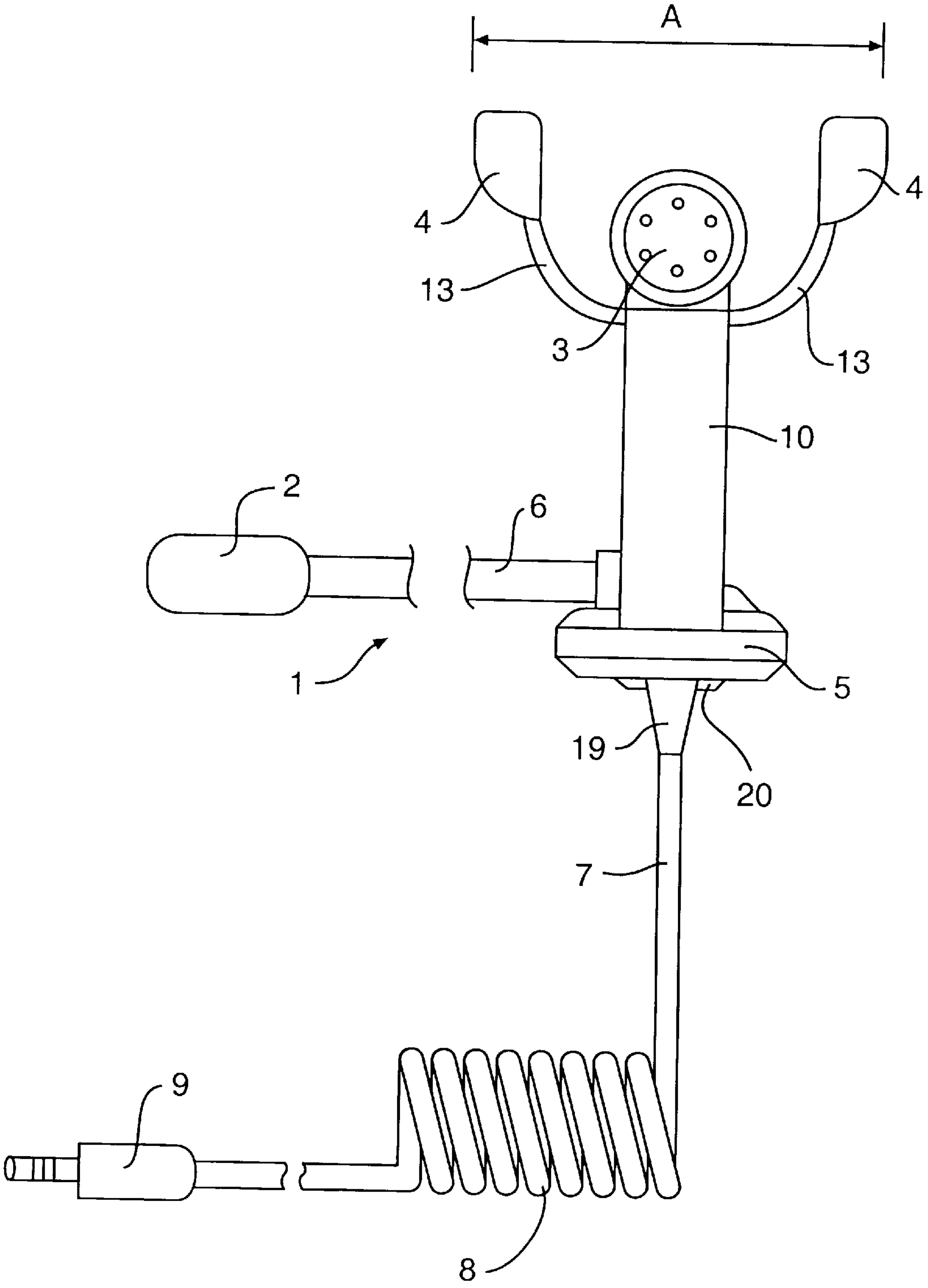
FIG. 1 shows a headset according to the invention from the direction of the earphone opening.

The headset includes the following parts: a flexible rod 6 connected to the center point of the coupling box 5 and terminating at a microphone 2 with muff, a bow part 10 connected to the coupling box 5 and at one end equipped with an earphone 3 and mounting arms 13 with support wings 4. The box 5 contains connecting wires from the earphone 3, the microphone 2, and a switch (key) 20, if any, to a radio connection cable 7. A protective rubber piece 19 together with other rubber gaskets guarantees the watertightness of the box 5. The protective rubber piece 19 also provides clamping for the cable 7.

The distance A between the ends of the support wings 4 is of essential importance for the mounting of the headset 1. This distance should be smaller than the largest dimension of the opening in the hearing protector padding and yet larger than the smaller dimension of the opening for mounting the headset 1 securely into position.

Figure 2:
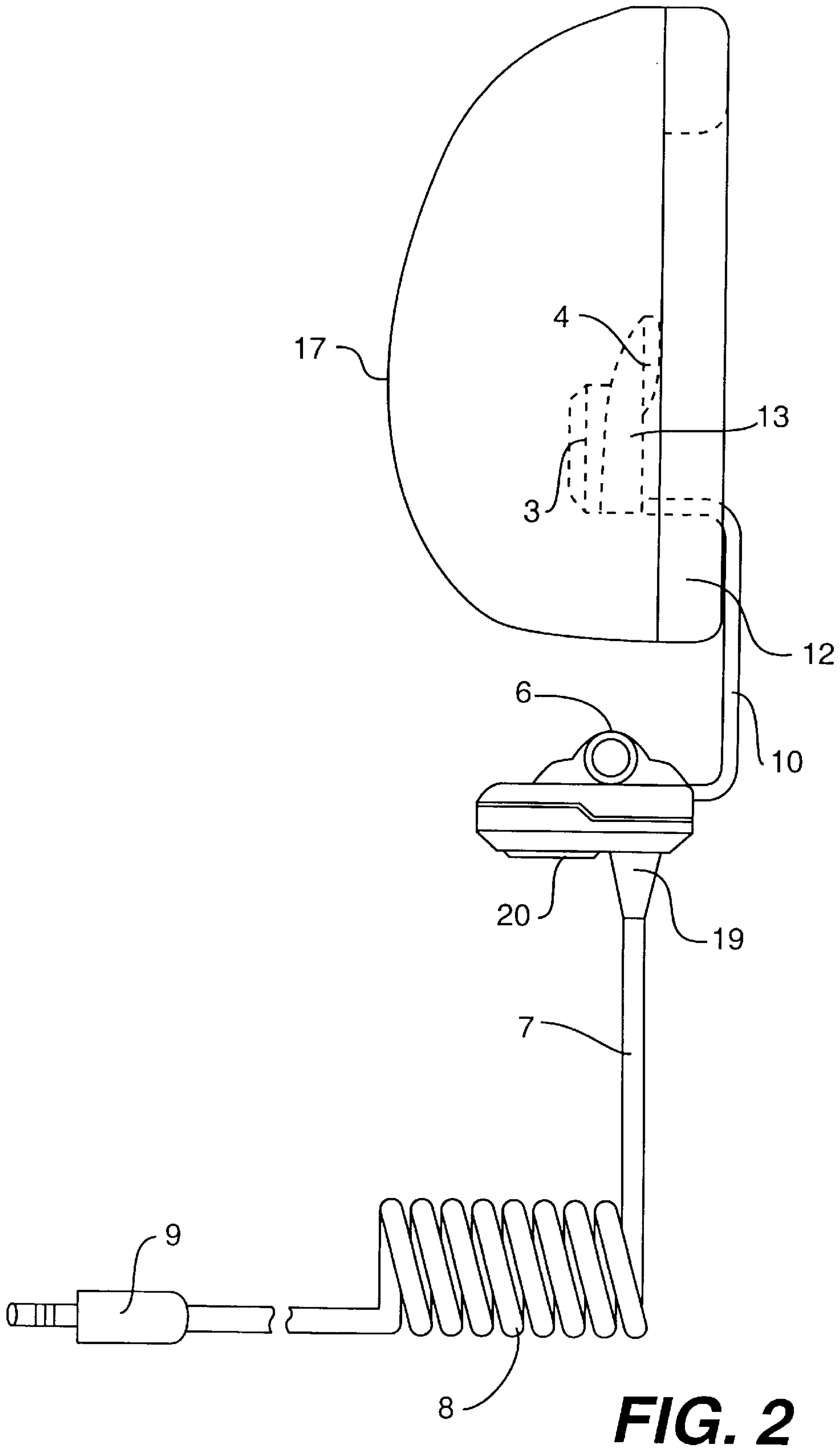
FIG. 2 shows the headset of FIG. 1 from the direction of the user's face.

As shown in FIG. 2, the bow part (10) is essentially U-shaped such that the U-shape as closely as possible follows the outer surface of the hearing protector padding 12. The bow part 10 can be relatively wide, 1–3 cm, but should, however, be dimensioned as thin as possible, 0.5–3 mm, so as to minimize acoustic leaks. The electrical connections are forwarded from the connection box 5 by means of a wire 7 which is advantageously provided with a screw part 8. The wire 7 is further provided with a connector 9 at its end, the connector enabling a control unit connection. The headset 1 is fixed to the hearing protector between the structure behind the hearing protector padding 12 and the cup 17 isolation material by means of support parts 4. The typically rigid structure behind the padding 12 can either be part of the padding 12 or, correspondingly, an integral part of the cup 17.

Figure 3:
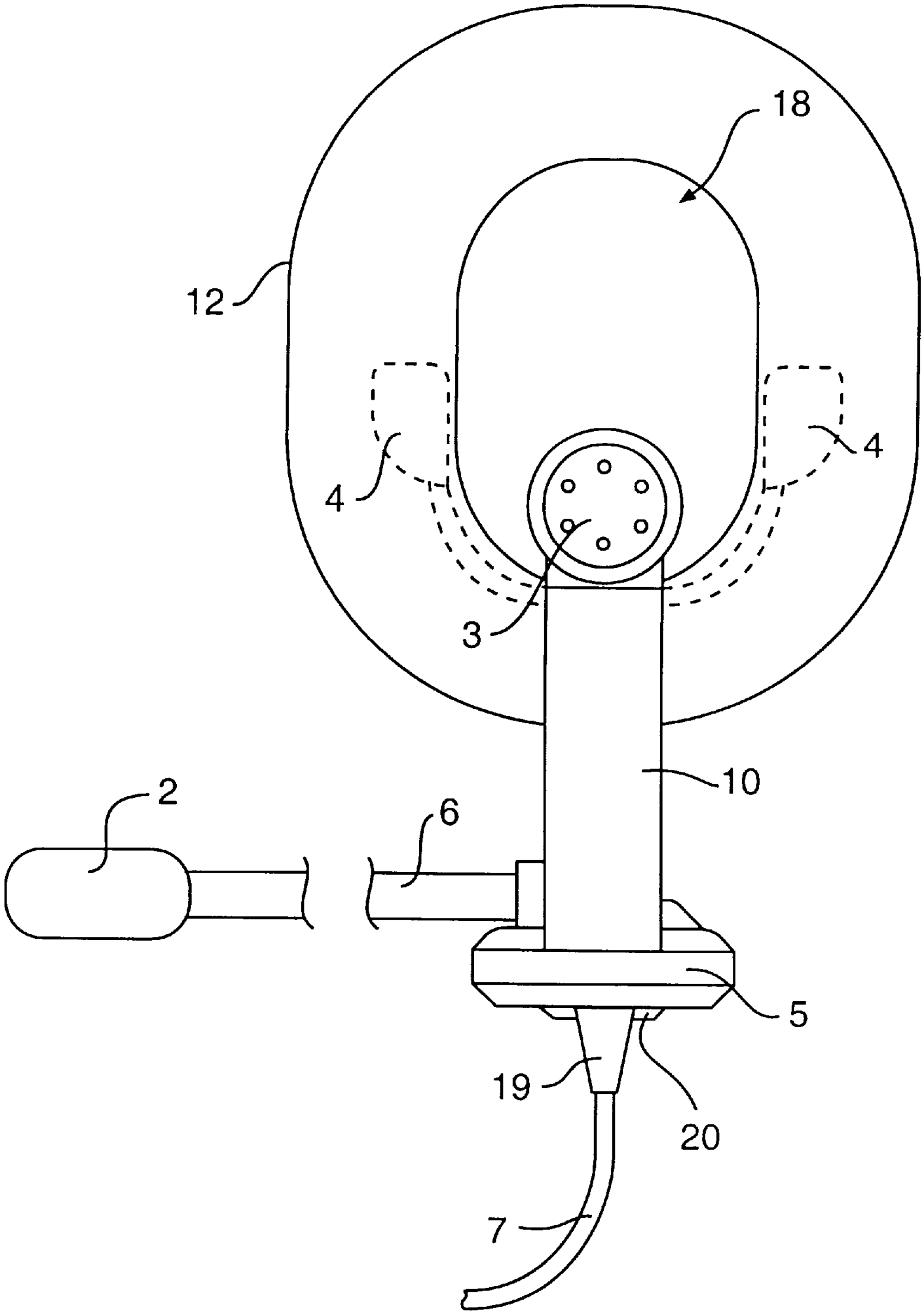
FIG. 3 shows the headset illustrated in FIGS. 1 and 2 seen as with a sideways position of the user's head and mounted into a hearing protector.

FIG. 3 shows the headset mounted behind the hearing protector padding 12, between the padding 12 and the isolation material of the protective cup. As seen in FIG. 3, the direction of the largest dimension of the mounting wing constituted by the mounting arms 13 and the support wings 4 should be approximately horizontal when the headset 1 is in position.

Figure 4:
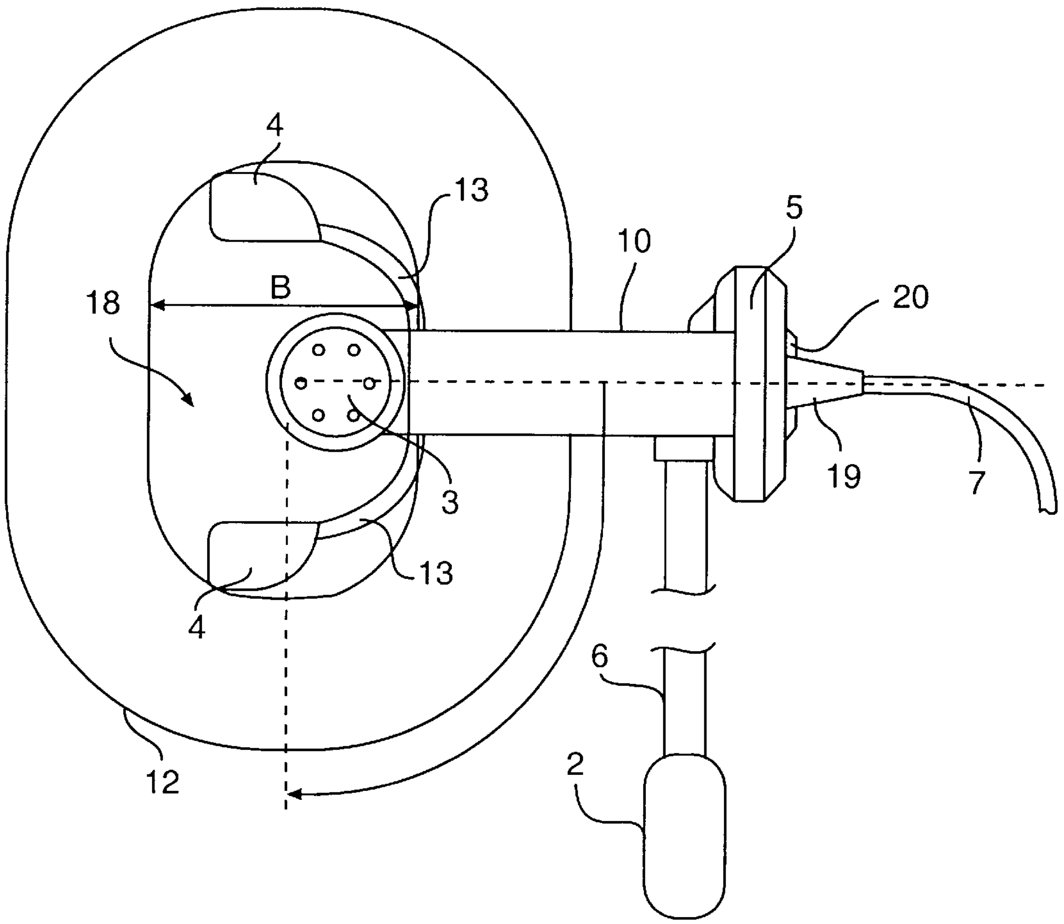
FIG. 4 illustrates the mounting in of the headset of FIG. 1 seen as with a sideways position of the user's head.

FIG. 4 illustrates how the mounting of the headset is based on the fact that the opening 18 provided for the user's ear in the padding 12 is, due to the basic measures of human anatomy, essentially elliptic so as to provide room for the ear in the opening 18. Dimension A in FIG. 1 of the mounting arms 13 and the support parts 4 is selected such that it is smaller than the longer dimension of the ear opening 18 and greater than the shorter dimension B. This provides for a mounting by pressing the mounting arms 13 and support parts 4 into the ear opening 18 in accordance with the figure in the direction of the longer axis and by thereafter turning the headset about 90°. Then the support parts 4 are secured into position behind the padding 12.

Figure 5:
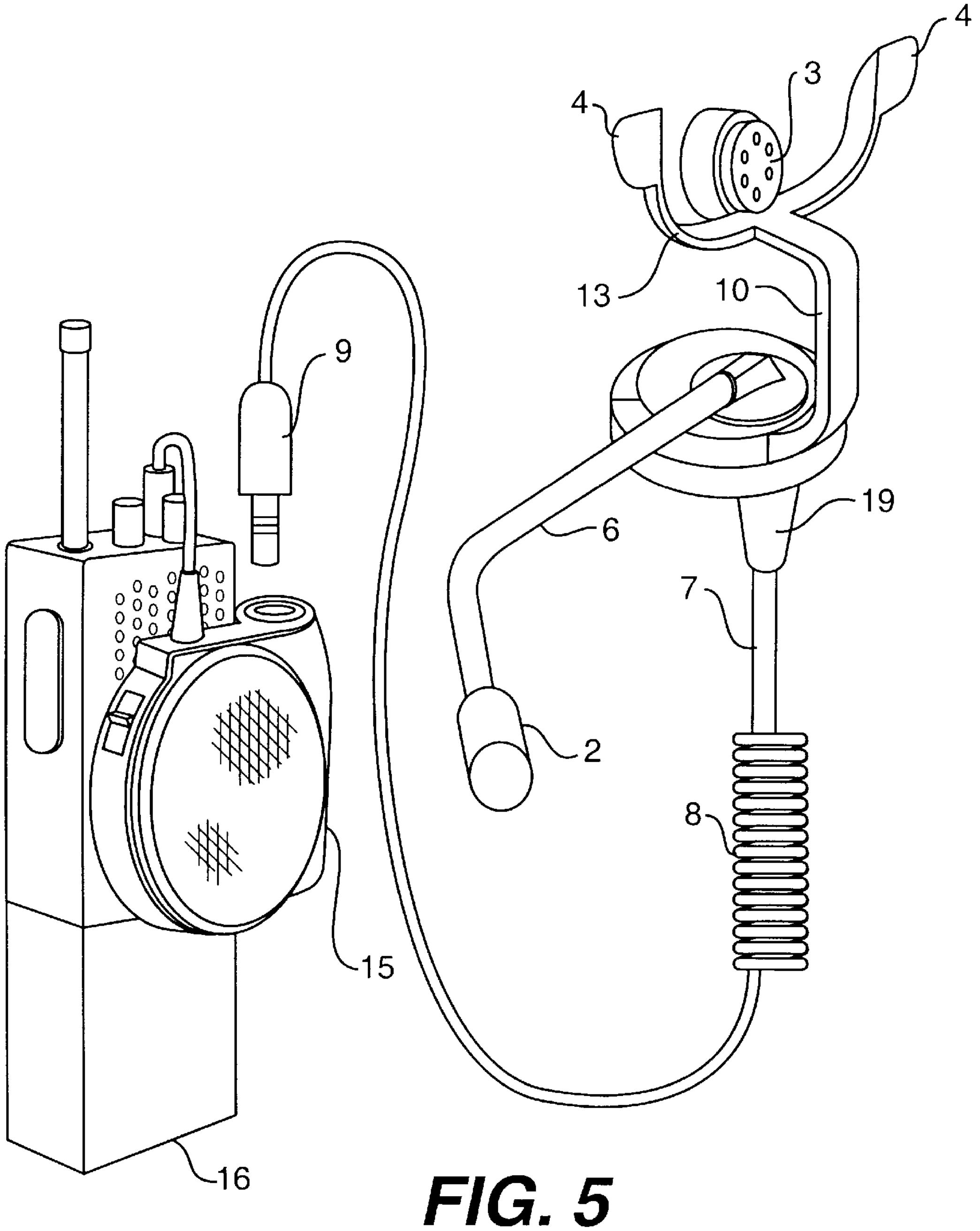
FIG. 5 is a perspective view of the headset according to the invention connected to an control unit and a radiotelephone.

As seen in FIG. 5, the headset is connected to a radiotelephone 16 either directly or via a control unit 15 provided with a separate transmitting button by means of a connection cable 7. The mounting wing 13 and 4 can in accordance with the figure form an integral unit with the bow part 10. Within the scope of the invention, the structure may also be of greater integration, whereby actual mounting arms 13 and support wings cannot be defined.

The mounting arms 13 and support parts 4 may naturally be attached directly to the earphone case 3.

The rod microphone in the microphone case of the headset according to the invention may at the manufacturing stage be replaced by another type of microphone such as a laryngophone, a bone microphone, or a collar microphone.

The invention being thus described, it will be obvious that the same may be varied in many ways. Such variations are not to be regarded as a departure from the spirit and scope of the invention, and all such modifications as would be obvious to one skilled in the art were intended to be included within the scope of the following claims.

I claim:

1. A communication headset which attaches to a hearing protector, the hearing protector including a padding part having first and second sides with a substantially elliptical ear opening, said communication headset comprising:

a microphone;

an earphone;

conductor wires connected and propagating signals to said earphone and from said microphone;

a substantially bow-shaped member supporting said microphone and said earphone, said bow-shaped member substantially enclosing a first side of the padding part; and means for mounting said microphone to the hearing protector, said means for mounting including projections which contact a second side of the padding part while said bow-shaped member penetrates through the ear opening, said bow-shaped member and said mounting means are initially placed in the ear opening and are rotated to facilitate installation of said communication headset in the hearing protector without substantial structural modification of the hearing protector.

2. The communication headset of claim 1, wherein said projections include mounting arms and support wings, each wing including a mounting arm, and a distance between a pair of wings is substantially larger than a minimum dimension of the ear opening and smaller than a maximum dimension of the ear opening, whereby said microphone is mounted in the ear opening upon rotation of the pair of wings which are initially oriented with the maximum dimension of the ear opening and oriented with the minimum dimension after rotation.

3. The communication headset of claim 1, wherein said bow-shaped member is also substantially U-shaped.

4. The communication headset of claim 1, wherein said bow-shaped member further includes a coupling device connected to at least one of said conductor wires.

* * * * *